United States Patent
Andersch et al.

(10) Patent No.: US 8,865,622 B2
(45) Date of Patent: Oct. 21, 2014

(54) USE OF ACTIVE INGREDIENTS FOR CONTROLLING NEMATODES IN NEMATODE-RESISTANT CROPS

(75) Inventors: Wolfram Andersch, Bergisch Gladbach (DE); Bill Striegel, Cary, NC (US); Kevin Bugg, Raleigh, NC (US); Steven Riniker, Seffner, NC (US); Nalini Desai, Chapel Hill, NC (US); Candace Poutre, Moncure, NC (US)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/818,652

(22) PCT Filed: Sep. 21, 2011

(86) PCT No.: PCT/EP2011/066448
§ 371 (c)(1),
(2), (4) Date: May 10, 2013

(87) PCT Pub. No.: WO2012/038476
PCT Pub. Date: Mar. 29, 2012

(65) Prior Publication Data
US 2013/0232645 A1 Sep. 5, 2013

Related U.S. Application Data

(60) Provisional application No. 61/419,433, filed on Dec. 3, 2010, provisional application No. 61/418,520, filed on Dec. 1, 2010, provisional application No. 61/385,247, filed on Sep. 22, 2010.

(30) Foreign Application Priority Data

Dec. 1, 2010 (EP) ..................................... 10193328
Dec. 1, 2010 (EP) ..................................... 10193341

(51) Int. Cl.
*A01N 25/26* (2006.01)
*A01N 43/40* (2006.01)
*A01N 63/04* (2006.01)
*A01N 63/00* (2006.01)

(52) U.S. Cl.
CPC ................ *A01N 63/04* (2013.01); *A01N 43/40* (2013.01); *A01N 63/00* (2013.01)
USPC ........................................... 504/100; 504/244

(58) Field of Classification Search
CPC ....................................................... A01N 43/40
See application file for complete search history.

(56) References Cited

U.S. PATENT DOCUMENTS

| 7,572,818 B2 | 8/2009 | Mansfield et al. | |
|---|---|---|---|
| 2005/0234110 A1 | 10/2005 | Mansfield et al. | |
| 2010/0249193 A1* | 9/2010 | Andersch et al. | 514/341 |
| 2011/0105577 A1* | 5/2011 | Meissner et al. | 514/384 |
| 2012/0083463 A1* | 4/2012 | Maue et al. | 514/30 |
| 2013/0097728 A1* | 4/2013 | Heinrichs et al. | 800/279 |
| 2013/0324400 A1* | 12/2013 | Riggs et al. | 504/100 |

FOREIGN PATENT DOCUMENTS

| EP | 2039772 | * | 3/2009 |
|---|---|---|---|
| EP | 2132987 | * | 12/2009 |
| WO | 2004016088 | | 2/2004 |
| WO | WO 2004016088 | * | 2/2004 |

OTHER PUBLICATIONS

International Search Report of PCT/EP2011/066448 Mailed Jan. 26, 2012.

\* cited by examiner

*Primary Examiner* — Alton Pryor
(74) *Attorney, Agent, or Firm* — Miles & Stockbridge, P.C.

(57) ABSTRACT

The present invention relates generally to the use of fluopyram and compositions comprising fluopyram for controlling nematodes in nematode resistant crops and/or increasing crop yield and to methods particularly useful for controlling nematodes and/or increasing crop yield in those crops.

18 Claims, 2 Drawing Sheets

USE OF ACTIVE INGREDIENTS FOR CONTROLLING NEMATODES IN NEMATODE-RESISTANT CROPS

CROSS REFERENCE TO RELATED APPLICATIONS

This application is a §371 National Stage Application of PCT/EP2011/066448 filed Sep. 21, 2011, which claims priority to European Application Nos. 10193328.1, filed Dec. 1, 2010 and 10193341.4, filed Dec. 1, 2010 and U.S. Provisional Application No. 61/385,247, filed Sep. 22, 2010, 61/418,520, filed Dec. 1, 2010 and 61/419,433, filed Dec. 3, 2010.

BACKGROUND OF THE INVENTION

1. Field of the Invention

The present invention relates generally to the use of N-{2-[3-chloro-5-(trifluoromethyl)-2-pridinyl]ethyl}-2-(trifluoromethyl)benzamide(fluopyram) for controlling nematodes in nematode resistant crops and to methods particularly useful for controlling nematodes and/or increasing crop yield in those crops.

2. Description of Related Art

Fluopyram is defined to be the compound of the formula (I)

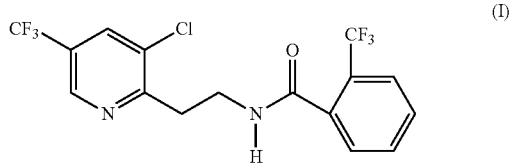 [SMILES: O=C(NCCc1ncc(C(F)(F)F)cc1Cl)c1ccccc1C(F)(F)F]

as well as the N-oxides of the compound thereof.

Fluopyram is a broad spectrum fungicide with penetrant and translaminar properties for foliar, drip, drench and seed treatment applications on a wide range of different crops against many economically important plant diseases. It is very effective in preventative applications against powdery mildew species, grey mould and white mould species. It has an efficacy against many other plant diseases. Fluopyram has shown activity in spore germination, germ tube elongation and mycelium growth tests. At the biochemical level, fluopyram inhibits mitochondrial respiration by blocking the electron transport in the respiratory chain of Succinate Dehydrogenase (complex II-SDH inhibitor).

Fluopyram and its manufacturing process starting from known and commercially available compounds is described in EP-A-1 389 614 and WO 2004/016088.

A general description of the nematicidal activity of pyridylethylbenzamide derivatives is found in WO-A 2008/126922.

Nematodes are tiny, worm-like, multicellular animals adapted to living in water. The number of nematode species is estimated at half a million. An important part of the soil fauna, nematodes live in a maze of interconnected channels, called pores, that are formed by soil processes. They move in the films of water that cling to soil particles. Plant-parasitic nematodes, a majority of which are root feeders, are found in association with most plants. Some are endoparasitic, living and feeding within the tissue of the roots, tubers, buds, seeds, etc. Others are ectoparasitic, feeding externally through plant walls. A single endoparasitic nematode can kill a plant or reduce its productivity. Endoparasitic root feeders include such economically important pests as the root-knot nematodes (*Meloidogyne* species), the reniform nematodes (*Rotylenchulus* species), the cyst nematodes (*Heterodera* species), and the root-lesion nematodes (*Pratylenchus* species). Direct feeding by nematodes can drastically decrease a plant's uptake of nutrients and water. Nematodes have the greatest impact on crop productivity when they attack the roots of seedlings immediately after seed germination. Nematode feeding also creates open wounds that provide entry to a wide variety of plant-pathogenic fungi and bacteria. These microbial infections are often more economically damaging than the direct effects of nematode feeding.

Generally nematode resistance is characterized by host plant cell death at or nearby the feeding site of the parasitic nematode. Particular resistance genes and nematode interaction influence the timing and localization of the resistance response. Williamson et al. (Trends in Genetics, Vol. 22, No. 7, July 2006) describes the nature and mechanisms of plant-nematode interactions with respect to resistance in plants.

Nematode-resistant plants can be related to three main approaches being nematode targets, nematode-crop interface and plant response. Antifeedant or nematicidal proteins, disruption of essential nematode gene expression by RNA interference, disruption of sensory function by RNA interference, peptides or plantibodies or nematicidal metabolites are examples for nematode targets; disruption of nematode pathogenicity factors regarding migration and invasion or regarding feeding site induction and maintenance by RNA interference, peptides or plantibodies, stealth or repellant plants; or the conversion of host plants to non-host plants are examples for nematode-crop interface while plant resistance gene or hypersensitive response activation by nematode invasion; Induced cell death or other site incompatibility by feeding site specific promoters or conversion of crops to tolerance are examples for plant response.

Although nematode-resistant plants are described to be resistant towards specific nematodes, there is still some interactions between the nematode and the crop which, due to the different defense reactions of the plant, might lead to a partially impaired plant. One example of these defense reactions is the hypersensitive response. One consequence might result in impaired roots and loss of vigor of the affected plants.

Current nematode control focuses essentially on the prevention of nematode attack on the plant. Once a plant is parasitized it is virtually impossible to kill the nematode without also destroying the plant. Therefore, it would be advantageous to provide enhanced nematode control compounds and methods of treating nematode resistant plants to prevent or reduce nematode damage.

A large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and also the germinating plant with a minimum of crop protection agents being employed.

SUMMARY

This invention now provides advantageous uses of fluopyram for controlling nematodes infesting nematode resistant crops and/or increasing yield.

DETAILED DESCRIPTION OF A PREFERRED EMBODIMENT

Figure 1:
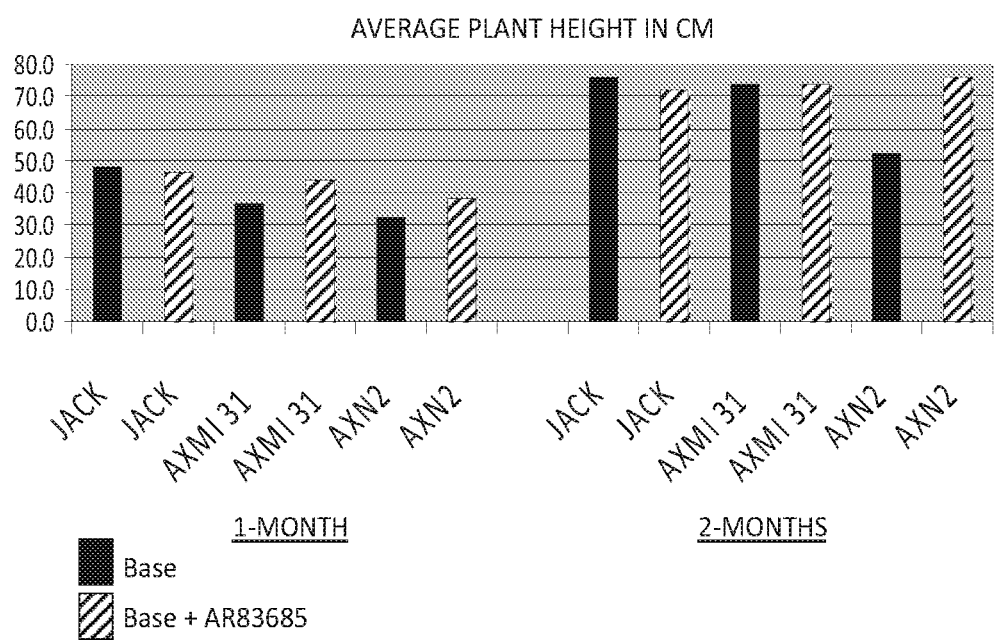
FIGS. 1 and 2 represent embodiments as described herein.

Accordingly, the present invention also relates to the use of compositions comprising fluopyram for controlling nematodes infesting nematode resistant crops and/or increasing yield.

Accordingly, the present invention also relates to the use of compositions comprising fluopyram for controlling nematodes infesting insect resistant crops.

Accordingly, the present invention also relates to the use of compositions comprising
A) fluopyram and
B) at least one agrochemically active compound,
for controlling nematodes infesting nematode resistant crops and/or increasing yield.

Accordingly, the present invention also relates to the use of compositions comprising
A) fluopyram and
B) at least one agrochemically active compound,
for controlling nematodes infesting insect resistant crops.

In a preferred embodiment the invention also relates to the use of compositions comprising
A) fluopyram and
B) the biological control agent *Bacillus firmus* strain CNCM I-1582, in particular the spores (U.S. Pat. No. 6,406,690) for controlling nematodes infesting nematode resistant crops and/or increasing yield.

In a preferred embodiment the invention also relates to the use of compositions comprising
A) fluopyram and
B) the biological control agent *Bacillus firmus* strain CNCM I-1582, in particular the spores (U.S. Pat. No. 6,406,690) for controlling nematodes infesting insect resistant crops.

An exemplary method of the invention comprises applying a fluopyram of the invention to either soil or a plant (e.g., seeds or foliarly) to control nematode damage and/or increase crop yield.

The present invention is drawn to compositions and methods for regulating pest resistance or tolerance in plants or plant cells. By "resistance" is intended that the pest (e.g., insect or nematode) is killed upon ingestion or other contact with the plant or parts thereof. By "tolerance" is intended an impairment or reduction in the movement, feeding, reproduction, or other functions of the pest. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

In conjunction with the present invention "controlling" denotes a preventive or curative reduction of the insect or nematode infestation in comparison to the untreated crop, more preferably the infestation is essentially repelled, most preferably the infestation is totally suppressed.

By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition.

The present invention also relates to a method for the protection of seed and germinating plants, or plant from attack by pests, by selectively applying pesticidal agents to the seed of a transgenic plant. Pesticidal agents include chemical or biological control agents compositions applied to the seed of the transgenic plant, wherein the agent is intended to provide protection of the plant or seed thereof against damage caused by one or more plant pests. Furthermore, the invention relates to seed which has been treated with a pesticidal agent as described herein. Application of a pesticidal agent to the seed of a transgenic plant results in an improved resistance or tolerance to one or more plant pests and/or improved yield or vigor compared to a transgenic plant cultivated from a seed not treated with a pesticidal agent as described herein, or a plant of the same species as the referenced transgenic plant that has been cultivated from a seed treated with a pesticidal agent as described herein but that lacks the transgene (either of which may be herein referred to as a "control" plant).

In some embodiments, treatment of the seed with these agents not only protects the seed itself, but also the resulting plants after emergence, from pests. In this manner, the immediate treatment of the crop at the time of sowing or shortly thereafter can be dispensed with.

DESCRIPTION OF THE PREFERRED EMBODIMENTS

The methods according to the present invention have been found to provide a greater degree of plant vigor and yield in nematode and fungal infested environments than would be expected from application of a biological or chemical control agent or the presence of an insect or nematode control gene alone. At least some of the insect control agents within the scope of the present invention have been shown to provide increased root mass even in the absence of insect pressure which increased root mass leads to improved establishment of the beneficial bacteria within the rhizosphere which, in turn, reduces overall losses in crop vigor and yields caused by either plant parasitic nematodes or fungi. Along with the physical combination of these components while treating plants and plant material, in one preferred embodiment of this invention, the compositions of the present invention have been formulated to provide a stable environment for living biological control agents such as spore-forming, root-colonizing bacteria. Various additives may be added to each inventive composition depending on the desired properties for a final formulation which has the necessary physical and chemical stability to produce a commercially viable product.

Nematode Resistant Plants

Fluopyram is particularly useful in controlling plant-parasitic nematodes in plants carrying one or more of the genes listed in Table 1. Fluopyram in combination with at least one agrochemically active compound is particularly useful in controlling plant-parasitic nematodes in plants carrying one more of the genes listed in Table 1. Fluopyram in combination with the biological control agent *Bacillus firmus* strain CNCM I-1582 is particularly useful in controlling plant-parasitic nematodes in plants carrying one or more of the genes listed in Table 1. The nucleotide and amino acid sequence information for each of these genes are represented by the SEQ ID NOs listed in columns 4 and 5 of Table 1 with respect to the United States Patent Application Serial No. listed in column 2 of Table 1.

| GENE NAME | U.S. APPLICATION SER. NO. | FILING DATE | NUCLEOTIDE SEQ ID NO | AMINO ACID SEQ ID NO |
|---|---|---|---|---|
| axmi205 | 12/828,594 | Jul. 1, 2010 | 1 | 2, 3, 4, 5, 6, 7, 8 |
| optaxmi205v01.03 | 12/828,594 | Jul. 1, 2010 | 10 | 2 |
| optaxmi205v01.02 | 12/828,594 | Jul. 1, 2010 | 9 | 2 |
| optaxmi205v01.04 | 12/828,594 | Jul. 1, 2010 | 11 | 2 |
| optaxmiR1(evo 21) | 12/701,058 | Feb. 5, 2010 | 12 | 13 |
| optaxmiR1(evo 22) | 12/701,058 | Feb. 5, 2010 | 14 | 15 |
| optaxmiR1(evo 23) | 12/701,058 | Feb. 5, 2010 | 16 | 17 |
| optaxmiR1(evo 26) | 12/701,058 | Feb. 5, 2010 | 18 | 19 |
| optaxmi115v01 | 12/497,221 | Jul. 2, 2009 | 15 | 6 |
| optaxmi115v02 | 12/497,221 | Jul. 2, 2009 | 16 | 6 |
| axmi115v02 | 61/471,848 | Apr. 15, 2008 | any of 1-14 | any of 15-31 |
| axmi100 | 12/491,396 | Jun. 25, 2009 | 36, 282 | 96 |
| axmi076 | 12/252,453 | Oct. 16, 2008 | 4, 6, 11 | 5 |
| axmi005 | 12/497,221 | Jul. 2, 2009 | 3, 7 | 4, 9 |
| optcry1Ac | 12/249,016 | Oct. 10, 2008 | 1, 2, 3, 4, 5 | 6 |
| axmi031 | 11/762,886 | Jun. 14, 2007 | 20 | 21 |
| axn2 | 12/638,591 | Dec. 15, 2009 | 7, 10 | 8 |

Fluopyram is particularly useful in controlling plant-parasitic nematodes in plants carrying one or more of the genes listed in Table 1. Fluopyram in combination with at least one agrochemically active compound is particularly useful in controlling plant-parasitic nematodes in plants carrying one or more of the genes listed in Table 1. Fluopyram in combination with the biological control agent *Bacillus firmus* strain CNCM I-1582 is particularly useful in controlling plant-parasitic nematodes in plants carrying one or more of the genes listed in Table 1.

Fluopyram or fluopyram in combination with the biological control agent *Bacillus firmus* strain CNCM I-1582 or fluopyram in combination with at least one agrochemically active compound is particularly useful in controlling plant-parasitic nematodes in plants carrying one or more of the genes as described in the following documents: WO2009/027539A2, WO2009/027313A2, WO2008/152008A2, WO2008/110522A1, WO2008/095972A1, WO2008/095970A1, WO2008/095969A1, WO2008/095919A1, WO2008/095916A1, WO2008/095911A2, WO2008/095910A1, WO2008/095889A1, WO2008/095886A1, WO2008/077892A1, WO2008/071726A2, WO2006/020821A2, WO2005/082932A2, WO2009/048847A1, WO2007/095469A2, WO2005/012340A1, WO2007/104570A2, Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Fluopyram or fluopyram in combination with the biological control agent *Bacillus firmus* strain CNCM I-1582 or fluopyram in combination with at least one agrochemically active compound is particularly useful in controlling plant-parasitic nematodes in plants carrying one or more of the following genes Hs1$^{pro-1}$, Mi-1, Mi-1.2, Hero A, Gpa2, Gro1-4, Rhg1, Rhg4, Mi-3, Mi-9, Cre1, Cre3, Ma, Hsa-1$^{Og}$, Me3, Rmc1, CLAVATA3-like peptides (e.g. SYV46).

A preferred embodiment comprises the nematode-resistant plant as described above treated with Fluopyram.

A preferred embodiment comprises the nematode-resistant plant as described above treated with Fluopyram in combination with the biological control agent *Bacillus firmus* strain CNCM I-1582.

A preferred embodiment comprises the nematode-resistant plant as described above treated with Fluopyram in combination with at least one agrochemically active compound.

In various embodiments, the compositions and methods of the present invention comprise treatment of a transgenic plant comprising one or more of the genes listed in Table 1 with Fluopyram or fluopyram in combination with the biological control agent *Bacillus firmus* strain CNCM I-1582 or fluopyram in combination with at least one agrochemically active compound. In particular embodiments, Fluopyram or fluopyram in combination with the biological control agent *Bacillus firmus* strain CNCM I-1582 or fluopyram in combination with at least one agrochemically active compound is applied to the seed of the transgenic plant comprising one or more of the genes listed in Table 1, including biologically-active variants and fragments thereof.

An exemplary method of the invention comprises applying Fluopyram or fluopyram in combination with the biological control agent *Bacillus firmus* strain CNCM I-1582 or fluopyram in combination with at least one agrochemically active compound of the invention to propagation material (e.g seeds) of plants to combat nematode damage and/or increase crop yield.

A further exemplary method of the invention comprises applying Fluopyram or fluopyram in combination with the biological control agent *Bacillus firmus* strain CNCM I-1582 or fluopyram in combination with at least one agrochemically active compound to either soil or a plant (e.g. foliarly) to combat nematode damage and/or increase crop yield.

In various embodiments, the nematicidal biological control agent is fluopyram, and the nematode resistant crop comprises a transgenic plant comprising Axmi031 or Axn2 (Table 1).

The nucleotide and amino acid SEQ ID NOs listed in Table 1 are exemplary sequences and not intended to limit the scope of the invention. The invention encompasses plants and plant parts, including plant cells and seed, comprising one or more of the genes listed in column 1 of Table 1. In some embodiments, the invention encompasses plants and plant parts, including plant cells and seed, comprising one or more nucleotide sequences listed in column 4 of Table 1. In some embodiments, the invention encompasses plants and plant parts, including plant cells and seed, comprising one or more nucleotide sequences encoding one or more of the polypeptides listed in column 5 of Table 1.

In yet another embodiment, the invention encompasses plants and plant parts, including plant cells and seed, comprising one or more nucleotide sequences encoding a biologically-active variant or fragment of the amino acid sequence(s) listed in column 5 of Table 1.

A fragment of a nucleotide sequence that encodes a biologically active portion of a pesticidal protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein listed in Table 2 herein. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to the amino acid sequence listed in Table 2. In some embodiments, the fragments encompassed herein result from the removal of the C-terminal crystallization domain, e.g., by proteolysis or by insertion of a stop codon in the coding sequence.

Preferred pesticidal proteins of the present invention are encoded by a nucleotide sequence sufficiently identical to the nucleotide sequence(s) listed in Table 2, or are pesticidal proteins that are sufficiently identical to the amino acid sequence(s) listed in Table 2. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (e.g., a sequence listed in Table 2). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

"Variants" of the amino acid sequences listed in Table 2 include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543: Ge et al. (1991) *J. Biol. Chem.* 266:17954-17958; Schnepf et al. (1990) *J. Biol. Chem.* 265: 20923-20930; Rang et al. 91999) *Appl. Environ. Microbiol.* 65:2918-2925).

Variants and fragments of the proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

In the present context, agrochemically active compounds are to be understood as meaning all substances which are or may be customarily used for treating plants. Fungicides, bactericides, insecticides, acaricides, nematicides, molluscicides, safeners, plant growth regulators and plant nutrients as well as biological control agents may be mentioned as being preferred.

Mixing Partners

The agrochemically active compound described under B) are the following active ingredients being fungicides which may be mentioned are:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl] 1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1 RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-{[4-(trifluoromethyl)pyridin-2-yl]oxy}phenyl)ethyl]quinazolin-4-amine (1210070-84-0) (WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16) picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (19899-14-8), (3.29) 5-methoxy-2-methyl-4-(2-{[({(1E)-1-[3-(trifluoromethyl)phenyl]ethylidene}amino)oxy]methyl})phenyl)-2,4-dihydro-3H-1,2,4-triazol-3-one, (3.30) methyl (2E)-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-

9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1.2.4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper (2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulphur and sulphur preparations including calcium polysulphide (7704-34-9), (5.31) thiram (137-26-8), (5.32) tolylfluanid (731-27-1), (5.33) zineb (12122-67-7) and (5.34) ziram (137-30-4).

(6) Compounds capable to induce a host defence, for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (WO2005070917).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (WO2005042474).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulphate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrine (1018-71-9) (EP-A 1559320), (15.47) tebufloquin (376645-78-2), (15.48) tecloflalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2- yl}carbonyl)amino]-6-methyl-4,9-dioxo-1,5-dioxonan-7-yl 2-methylpropanoate (517875-34-2) (WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6) (WO 2008013622), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0) (WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4) (WO2009094442), (15.75) 5-fluoro-2-[(4-methylbenzyl)oxy]pyrimidin-4-amine (1174376-25-0) (WO2009094442), (15.76) 5-methyl-6-octyl[1,2,4]triazolo[1.5-a]pyrimidin-7-amine, (15.77) ethyl (2Z)-3-amino-2-cyano-3-phenylprop-2-enoate, (15.78) N-(4-{[3-(4-chlorobenzyl)-1,2,4-thiadiazol-5-yl]oxy}-2,5-dimethylphenyl)-N-ethyl-N-methylimidoformamide (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-brom)-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5) (WO 2007014290), (15.90) pentyl {6-[({[(1-methyl-1H-tetrazol-5-yl)phenyl]methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds, for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide (known from WO 2004/058723), (16.7) 5-fluoro-1,3-dimethyl-N-[4'-(prop-1-yn-1-yl)biphenyl-2-yl]-1H-pyrazole-4-carboxamide (known from WO 2004/058723), (16.8) 2-chloro-N-[4'-(prop-1-yn-1-yl)biphenyl-2-yl]pyridine-3-carboxamide (known from WO 2004/058723), (16.9) 3-(difluoromethyl)-N-[4'-(3,3-dimethylbut-1-yn-1-yl)biphenyl-2-yl]-1-methyl-1H-pyrazole-4-carboxamide (known from WO 2004/058723), (16.10) N-[4'-(3,3-dimethylbut-1-yn-1-yl)biphenyl-2-yl]-5-fluoro-1,3-dimethyl-1H-pyrazole-4-carboxamide (known from WO 2004/058723), (16.11) 3-(difluoromethyl)-N-(4'-ethynylbiphenyl-2-yl)-1-methyl-1H-pyrazole-4-carboxamide (known from WO 2004/058723), (16.12) N-(4'-ethynylbiphenyl-2-yl)-5-fluoro-1,3-dimethyl-1H-pyrazole-4-carboxamide (known from WO 2004/058723), (16.13) 2-chloro-N-(4'-ethynylbiphenyl-2-yl)pyridine-3-carboxamide (known from WO 2004/058723), (16.14) 2-chloro-N-[4'-(3,3-dimethylbut-1-yn-1-yl)biphenyl-2-yl]pyridine-3-carboxamide (known from WO 2004/058723), (16.15) 4-(difluoromethyl)-2-methyl-N-[4'-(trifluoromethyl)biphenyl-2-yl]-1,3-thiazole-5-carboxamide (known from WO 2004/058723), (16.16) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (16.17) 2-chloro-N-[4'-(3-hydroxy-3-methylbut-1-yn-1-yl)biphenyl-2-yl]pyridine-3-carboxamide (known from WO 2004/058723), (16.18) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (16.19) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (16.20) 2-chloro-N-[4'-(3-methoxy-3-methylbut-1-yn-1-yl)biphenyl-2-yl]pyridine-3-carboxamide (known from WO 2004/058723), (16.21) (5-bromo-2-methoxy-4-methylpyridin-3-yl)(2,3,4-trimethoxy-6-methylphenyl)methanone (known from EP-A 1 559 320), (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate, N-[9-(dichloromethylene)-1,2,3,4-tetrahydro-1,4-methanonaphthalen-5- yl]-3-(difluoromethyl)-1-methyl-1H-pyrazole-4-carboxamide and 3-difluoromethyl-1-methyl-1H-pyrazole-4-carboxylic acid [2-(2,4-dichlorophenyl)-2-methoxy-1-methyl-ethyl]-amide.

Wherein all named mixing partners of the classes (1) to (16) can, if their functional groups enable this, optionally form salts with suitable bases or acids:

Being bactericides which may be mentioned are:
bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

being insecticides, acaricides and nematicides which may be mentioned are:

(1) Acetylcholinesterase (AChE) inhibitors, for example carbamates, e.g. alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, and xylylcarb; or organophosphates, e.g. acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlrfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl, O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, and imicyafos.

(2) GABA-gated chloride channel antagonists, for example organochlorines, e.g. camphechlor, chlordane, endosulfan, gamma-HCH, HCH, heptachlor, lindane, and methoxychlor; or fiproles (phenylpyrazoles). e.g. acetoprole, ethiprole, fipronil, pyrafluprole, pyriprole, and vaniliprole.

(3) Sodium channel modulators/voltage-dependent sodium channel blockers, for example pyrethroids, e.g. acrinathrin, allethrin (d-cis-trans, d-trans), beta-cyfluthrin, bifenthrin, bioallethrin, bioallethrin S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin. ZXI 8901, pyrethrin (pyrethrum), eflusilanat; DDT; or methoxychlor.

(4) Nicotinergic acetylcholine receptor agonists/antagonists, for example chloronicotinyls, e.g. acetamiprid, clothianidin, dinotefuran, imidacloprid, imidaclothiz, nitenpyram, nithiazine, thiacloprid, thiamethoxam, AKD-1022; or nicotine, bensultap, cartap, thiosultap-sodium, and thiocylam.

(5) Allosteric acetylcholine receptor modulators (agonists), for example spinosyns, e.g. spinosad and spinctoram.

(6) Chloride channel activators, for example mectins/macrolides, e.g. abamectin, emamectin, emamectin benzoate, ivermectin, lepimectin, and milbemectin; or juvenile hormone analogues, e.g. hydroprene, kinoprene, methoprene, epofenonane, triprene, fenoxycarb, pyriproxifen, and diofenolan.

(7) Active ingredients with unknown or non-specific mechanisms of action, for example gassing agents, e.g. methyl bromide, chloropierin and sulfuryl fluoride; selective antifeedants, e.g. cryolite, pymetrozine, pyrifluquinazon and flonicamid; or mite growth inhibitors, e.g. clofentezine, hexythiazox, etoxazole.

(8) Oxidative phosphorylation inhibitors, ATP disruptors, for example diafenthiuron; organotin compounds, e.g. azocyclotin, cyhexatin and fenbutatin oxide; or propargite, tetradifon.

(9) Oxidative phoshorylation decouplers acting by interrupting the H proton gradient, for example chlorfenapyr, binapacryl, dinobuton, dinocap and DNOC.

(10) Microbial disruptors of the insect gut membrane, for example *Bacillus thuringiensis* strains.

(11) Chitin biosynthesis inhibitors, for example benzoylureas, e.g. bistrifluoron, chlorfluazuron, diflubenzuron, fluazuron, flucycloxuron, flufenoxuron, hexaflumuron, lufenuron, novaluron, novi-flumuron, penfluoron, teflubenzuron or triflumuron.

(12) Buprofezin.

(13) Moulting disruptors, for example cyromazine.

(14) Ecdysone agonists/disruptors, for example diacylhydrazines, e.g. chromafenozide, halofenozide, methoxyfenozide, tebufenozide, and Fufenozide (JS118); or azadirachtin.

(15) Octopaminergic agonists, for example amitraz.

(16) Site III electron transport inhibitors/site II electron transport inhibitors, for example hydramethylnon; acequinocyl; fluacrypyrim; or cyflumetofen and cyenopyrafen.

(17) Electron transport inhibitors, for example Site I electron transport inhibitors, from the group of the METI acaricides, e.g. fenazaquin, fenpyroximate, pyrimidifen, pyridaben, tebufenpyrad, tolfenpyrad, and rotenone; or voltage-dependent sodium channel blockers, e.g. indoxacarb and metaflumizone.

(18) Fatty acid biosynthesis inhibitors, for example tetronic acid derivatives, e.g. spirodiclofen and spiromesifen; or tetramic acid derivatives, e.g. spirotetramat.

(19) Neuronal inhibitors with unknown mechanism of action, e.g. bifenazate.

(20) Ryanodine receptor effectors, for example diamides, e.g. flubendiamide, (R),(S)-3-chloro-N'-{2-methyl-4-[1,2,2,2-tetrafluoro-1-(trifluoromethyl)ethyl]phenyl}-$N^2$-(1-methyl-2-methylsulphonyl-ethyl)phthalamide, chlorantraniliprole (Rynaxypyr), or Cyantraniliprole (Cyazypyr).

(21) Further active ingredients with unknown mechanism of action, for example amidoflumet, benclothiaz, benzoximate, bromopropylate, buprofezin, chinomethionat, chlordimeform, chlorobenzilate, clothiazoben, cycloprene, dicofol, dicyclanil, fenoxacrim, fentrifanil, flubenzimine, flufenerim, flutenzin, gossyplure, japonilure, metoxadiazone, petroleum, potassium oleate, pyridalyl, sulfluramid, tetrasul, triarathene or verbutine; or one of the following known active compounds 4-{[(6-bromopyrid-3-yl)methyl](2-fluoroethyl)amino}furan-2(5H)-one, 4-{[(6-fluoropyrid-3-yl)methyl](2,2-difluoroethyl)amino}furan-2(5H)-one, 4-{[(2-chloro-1,3-thiazol-5-yl)methyl](2-fluoroethyl)amino}furan-2(5H)-one, 4-{[(6-chloropyrid-3-yl)methyl](2-fluoroethyl)amino}furan-2(5H)-one, 4-{[(6-chloropyrid-3-yl)methyl](2,2-difluoroethyl)amino}furan-2(5H)-one (all known from WO 2007/115644), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](methyl)amino}furan-2(5H)-one, 4-{[(6-chloro-5-fluoropyrid-3-yl)methyl](cyclopropyl)amino}furan-2(5H)-one (both from WO 2007/115643), 4-{[(6-chloropyrid-3-yl)methyl](cyclopropyl)amino}furan-2(5H)-one, 4-{[(6-chloropyrid-3-yl)methyl](methyl)amino}furan-2(5H)-one (both from EP-A-0 539 588), [(6-chloropyridin-3-yl)methyl](methyl)oxido-$\lambda^4$-sulfanylidene cyanamide, [1-(6-chloropyridin-3-yl)ethyl](methyl)oxido-$\lambda^4$-sulfanylidene cyanamide (both from WO 2007/149134) and its diastereomers (A) and (B)

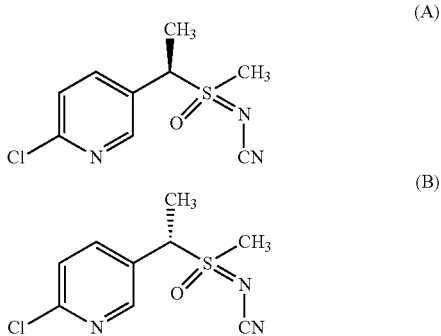

(also known from WO 2007/149134), [(6-trifluoromethylpyridin-3-yl)methyl](methyl)oxido-$\lambda^4$-sulfanylidene cyanamide (known from WO 2007/095229), or [1-(6-trifluoromethylpyridin-3-yl)ethyl](methyl)oxido-$\lambda^4$-sulfanylidene cyanamide (known from WO 2007/149134) and its diastereomers (C) and (D), namely Sulfoxaflor (also known from WO 2007/1491324)

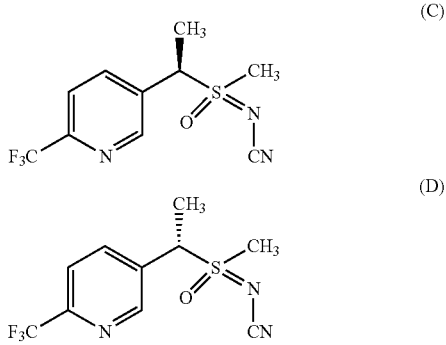

being molluscicides which may be mentioned are metaldehyde and methiocarb.

being safeners which may be mentioned are:

(1) Heterocyclic carboxylic acid derivates, for example dichlorophenylpyrazolin-3-carboxylic acid derivatives, e.g. 1-(2,4-dichlorophenyl)-5-(ethoxycarbonyl)-5-methyl-4,5-dihydro-1H-pyrazole-3-carboxylic acid, diethyl 1-(2,4-dichlorophenyl)-4,5-dihydro-5-methyl-1H-pyrazole-3,5-dicarboxylate ("mefenpyr-diethyl"), and similar compounds known from WO 91/07874; for example dichlorophenylpyrazolecarboxylic acid derivatives, e.g. ethyl 1-(2,4-dichlorophenyl)-5-methyl-1H-pyrazole-3-carboxylate, ethyl 1-(2,4-dichlorophenyl)-5-ispropyl-1H-pyrazole-3-carboxylate, ethyl 5-tert-butyl-1-(2,4-dichlorophenyl)-1H-pyrazole-3-carboxylate and similar compounds known from EP-A 0 333 131 and EP-A 0 269 806; for example 1,5-diphenylpyrazolo-3-carboxylic acid derivatives, e.g. ethyl 1-(2,4-dichlorophenyl)-5-phenyl-1H-pyrazole-3-carboxylate, methyl 1-(2-chlorophenyl)-5-phenyl-1H-pyrazole-3-carboxylate, and similar compounds known from EP-A 0 268 554; for example triazolecarboxylic acid derivatives, e.g. fenchlorazole, fenchlorazole-ethyl, and similar compounds known from EP-A 0 174 562 and EP-A 0 346 620; for example 2-isoxazoline-3-carboxylic acid derivatives, e.g. ethyl 5-(2,4-dichlorobenzyl)-4,5-dihydro-1,2-oxazole-3-carboxylate, ethyl 5-phenyl-4,5-dihydro-1,2-oxazole-3-carboxylate and similar compounds known from WO 91/08202, or 5,5-diphenyl-4,5-dihydro-1,2-oxazole-3-carboxylic acid, ethyl 5,5-diphenyl-4,5-dihydro-1,2-oxazole-3-carboxylate ("isoxadifen-ethyl"), propyl 5,5-diphenyl-4,5-dihydro-1,2-oxazole-3-carboxylate, ethyl 5-(4-fluorophenyl)-5-phenyl-4,5-dihydro-2-oxazole-3-carboxylate known from WO 95/07897.

(2) Derivatives of 8-quinolinol, for example derivatives of (quinolin-8-yloxy)acetic acid, e.g. heptan-2-yl[(5-chloroquinolin-8-yl)oxy]acetate ("cloquintocet-mexyl"), 4-methylpentan-2-yl[(5-chloroquinolin-8-yl)oxy]acetate, 4-(allyloxy)butyl[(5-chloroquinolin-8-yl)oxy]acetate, 1-(allyloxy)propan-2-yl[(5-chloroquinolin-8-yl)oxy]acetate, ethyl[(5-chloroquinolin-8-yl)oxy]acetate, methyl[(5-chloroquinolin-8-yl)oxy]acetate, allyl[(5-chloroquinolin-8-yl)oxy]acetate, 2-{[propylideneamino]oxy}ethyl[(5-chloroquinolin-8-yl)oxy]acetate, 2-oxopropyl[(5-chloroquinolin-8-yl)oxy]acetate, and similar compounds known from EP-A 0 086 750, EP-A 0 094 349, EP-A 0 191 736 or EP-A 0 492 366, as well as [(5-chloroquinolin-8-yl)oxy]acetic acid, its hydrates and salts, e.g. the lithium, sodium, potassium, calcium, magnesium, aluminum, iron, ammonium, quartanary ammonium, sulfonium or phosphonium salts as known from WO 02/34048; for example derivatives of [(5-chloroquinolin-8-yl)oxy]malonic acid, e.g diethyl[(5-chloroquinolin-8-yl)oxy]malonate, diallyl[(5-chloroquinolin-8-yl)oxy]malonate, ethyl methyl [(5-chloroquinolin-8-yl)oxy]malonate, and similar compounds known from EP-A 0 582 198.

(3) Dichloroacetamides, which are often used as pre-emergence safeners (soil active safeners), e.g. "dichlormid" (N,N-diallyl-2,2-dichloroacetamide), "R-29148" (3-dichloroacetyl-2,2,5-trimethyl-1,3-oxazolidine) and "R-28725" (3-dichloroacetyl-2,2-dimethyl-1,3-oxazolidine) both of the company Stauffer, "benoxacor" (4-dichloroacetyl-3,4-dihydro-3-methyl-2H-1,4-benzoxazine), "PPG-1292" (N-allyl-N-[(1,3-dioxolan-2-yl)-methyl]-dichloroacetamide) of PPG Industries, "DKA-24" (N-allyl-N-[(allylaminocarbonyl)methyl]-dichloroacetamide) of Sagro-Chem, "AD-6T" or "MON 4660" (3-dichloroacetyl-1-oxa-3-aza-spiro[4,5]decane) of Nitrokemia and Monsanto, "TI-35" (1-dichloroacetyl-azepane) of TRI-Chemical RT, "diclonon" (dicyclonon) or "BAS145138" or "LAB145138" (3-dichloroacetyl-2,5,5-trimethyl-1,3-diazabicyclo[4.3.0]nonane) of BASF, "Furilazol" or "MON 13900" [(RS)-3-dichloroacetyl-5-(2-furyl)-2,2-dimethyloxazolidine], as well as there (R)-isomer.

(4) Acylsulfonamides, for example N-acylsulfonamide of the formula (II)

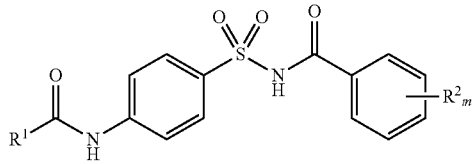

or its salts (known from WO 97/45016), wherein
$R^1$ represents $(C_1-C_6)$alkyl, which is unsubstituted or mono- to trisubstituted by substituents selected from the group consisting of halogen, $(C_1-C_4)$alkoxy, $(C_1-C_6)$haloalkoxy and $(C_1-C_4)$alkylthio;
$R^2$ represents halogen, $(C_1-C_4)$alkyl, $(C_1-C_4)$alkoxy, $CF_3$;
m is 1 or 2;
or for example 4-(benzoylsulfamoyl)benzamides of the formula (III)

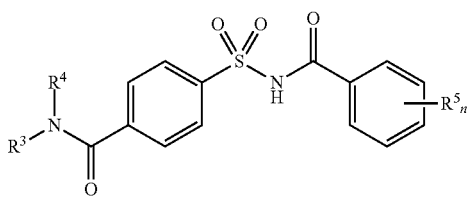

or its salts (known from WO 99/16744), wherein
$R^3$, $R^4$ independently of one another represent hydrogen, $(C_1-C_6)$alkyl, $(C_3-C_6)$alkenyl, $(C_3-C_6)$alkynyl, $(C_3-C_6)$cycloalkyl,
$R^5$ represents halogen, $(C_1-C_4)$alkyl, $(C_1-C_4)$haloalkyl or $(C_1-C_4)$alkoxy
n is 1 or 2,
in particular compounds of formula (III), wherein
$R^3$=cyclopropyl, $R^4$=hydrogen and $R^5{}_n$=2-OMe, ("cyprosulfamide"),
$R^3$=cyclopropyl, $R^4$=hydrogen and $R^5{}_n$=5-Cl-2-OMe,
$R^3$=ethyl, $R^4$=hydrogen and $R^5{}_n$=2-OMe,
$R^3$=isopropyl, $R^4$=hydrogen and $R^5{}_n$=5-Cl-2-OMe,
$R^3$=isopropyl, $R^4$=hydrogen and $R^5{}_n$=2-OMe.
or for example benzoylsulfamoylphenylureas of the formula (IV)

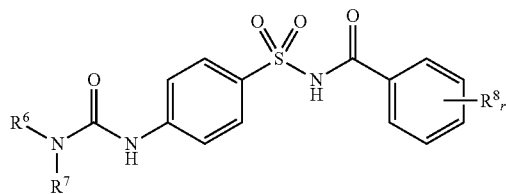

(known from EP-A 0 365 484), wherein
$R^6$, $R^7$ independently of one another represent hydrogen, $(C_1-C_8)$alkyl, $(C_3-C_6)$alkenyl, $(C_3-C_6)$alkynyl,
$R^8$ represents halogen, $(C_1-C_4)$alkyl, $(C_1-C_4)$alkoxy, $CF_3$
r is 1 or 2;

in particular
1-[4-(N-2-methoxybenzoylsulfamoyl)phenyl]-3-methyl urea,
1-[4-(N-2-methoxybenzoylsulfamoyl)phenyl]-3,3-dimethyl urea,
1-[4-(N-4,5-dimethylbenzoylsulfamoyl)phenyl]-3-methyl urea.

(5) Hydroxyaromatic compounds and aromatic-aliphatic carboxylic acid derivatives, e.g. ethyl 3,4,5-triacetoxybenzoate, 4-hydroxy-3,5-dimethoxybenzoic acid, 3,5-dihydroxybenzoic acid, 2,4-dihydroxybenzoic acid, 4-fluoro-2-hydroxybenzoic acid, 2-hydroxycinnamic acid, 2,4-dichlorocinnamic acid (cf. WO 2004/084631, WO 2005/015994, WO 2005/016001).

(6) 1,2-Dihydrochinoxalin-2-ones, e.g. 1-methyl-3-(2-thienyl)-1,2-dihydrochinoxalin-2-one, 1-methyl-3-(2-thienyl)-1,2-dihydrochinoxalin-2-thione, 1-(2-aminoethyl)-3-(2-thienyl)-1,2-dihydrochinoxalin-2-one hydrochlorid, 1-(2-methylsulfonylaminoethyl)-3-(2-thienyl)-1,2-dihydrochinoxalin-2-one (cf. WO 2005/112630).

(7) Diphenylmethoxyacetic acid derivatives, e.g. methyl (diphenylmethoxy)acetate (CAS-Reg. No. 41858-19-9), ethyl (diphenylmethoxy)acetate or (diphenylmethoxy)acetic acid (cf. WO 98/38856).

(8) Compounds of formula (V)

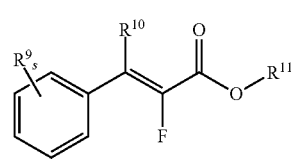

or its salts (known from WO 98/27049), wherein
$R^9$ represents halogen, $(C_1-C_4)$alkyl, $(C_1-C_4)$haloalkyl, $(C_1-C_4)$alkoxy, $(C_1-C_4)$haloalkoxy,
$R^{10}$ represents hydrogen or $(C_1-C_4)$alkyl,
$R^{10}$ represents hydrogen, in each case unsubstituted or mono- to trisubstituted $(C_1-C_8)$alkyl, $(C_2-C_4)$alkenyl, $(C_2-C_4)$alkynyl, or aryl, where the substituents are selected from the group consisting of halogen and $(C_1-C_8)$alkoxy,
s is 0, 1 or 2.

(9) 3-(5-Tetrazolylcarbonyl)-2-chinolones, e.g. 1,2-dihydro-4-hydroxy-1-ethyl-3-(5-tetrazolyl-carbonyl)-2-chinolone (CAS-Reg. No. 219479-18-2), 1,2-dihydro-4-hydroxy-1-methyl-3-(5-tetrazolyl-carbonyl)-2-chinolone (CAS-Reg. No. 95855-00-8) (cf. WO 99/00020).

(10) Compounds of the formulae (VI-a) and (VI-b)

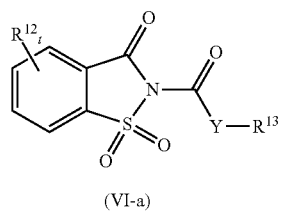

(VI-a)

-continued

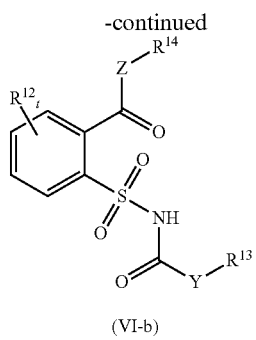

(VI-b)

(known from WO 2007/023719 and WO 2007/023764), wherein $R^{12}$ represents halogen, ($C_1$-$C_4$)alkyl, methoxy, nitro, cyano, $CF_3$, $OCF_3$, Y, Z independently represent O or S, t is 0, 1, 2, 3 or 4, $R^{13}$ represents ($C_1$-$C_{16}$)alkyl, ($C_2$-$C_6$)alkenyl, aryl, benzyl, halogenobenzyl, $R^{14}$ represents hydrogen or ($C_1$-$C_6$)alkyl.

(11) Oxyimino compounds, known as seed treatment agents, e.g. "oxabetrinil" [(Z)-1,3-dioxolan-2-ylmethoxyimino(phenyl)acetonitril], "fluxofenim" [1-(4-chlorophenyl)-2,2,2-trifluoro-1-ethanone-O-(1,3-dioxolan-2-ylmethyl)-oxime], and "cyometrinil" or "CGA-43089" [(Z)-cyanomethoxy-imino (phenyl)acetonitril], all known as seed treatment safener for sorghum against damage by metolachlor.

(12) Isothiochromanones, e.g. methyl[(3-oxo-1H-2-benzothiopyran-4(3H)-ylidene)methoxy]acetate (CAS-Reg. No. 205121-04-6) and similar compounds known from WO 98/13361.

(13) Compounds from the group consisting of "naphthalic anhydrid" (1,8-naphthalenedicarboxylic acid anhydride), which is known as seed treatment safener for corn (maize) against damage by thiocarbamate herbicides, "fenclorim" (4,6-dichloro-2-phenylpyrimidine), which is known as seed treatment safener in sown rice against damage by pretilachlor, "flurazole" (benzyl-2-chloro-4-trifluoromethyl-1,3-thiazol-5-carboxylate), which is known as seed treatment safener for sorghum against damage by alachlor and metolachlor, "CL 304415" (CAS-Reg. No. 31541-57-8), (4-carboxy-3,4-dihydro-2H-1-benzopyran-4-acetic acid) of American Cyanamid, which is known as safener for corn (maize) against damage by imidazolinones, "MG 191" (CAS-Reg. No. 96420-72-3) (2-dichloromethyl-2-methyl-1,3-dioxolane) of Nitrokemia, known as safener for corn (maize), "MG-838" (CAS-Reg. No. 133993-74-5), (2-propenyl 1-oxa-4-azaspiro[4.5]decane-4-carbodithioate) of Nitrokemia, "Disulfoton" (O,O-diethyl-S-2-ethylthioethyl phosphorodithioate), "dietholate" (O,O-diethyl-O-phenylphosphorothioate), "mephenate" (4-chlorophenyl-methylcarbamate).

(14) Compounds, which besides herbicidal activity als exhibit Safener activity in crops like rice, e.g. "Dimepiperate" or "MY-93" (S-1-methyl-1-phenylethyl-piperidin-1-carbothioate), which is known as safener for rice against damage by molinate, "daimuron" or "SK 23" [1-(1-methyl-1-phenylethyl)-3-p-tolyl-urea], which is known as safener for rice against damage by imazosulfuron. "cumyluron"="JC-940" [3-(2-chlorophenylmethyl)-1-(1-methyl-1-phenyl-ethyl) urea](cf. JP-A 60-087254), which is known as safener for rice against damage by some herbicides, "methoxyphenon" or "NK 049" (3,3'-dimethyl-4-methoxy-benzophenone), which is known as safener for rice against damage by some herbicides, "CSB" [1-bromo-4-(chloromethylsulfonyl)benzene] of Kumiai (CAS-Reg. No. 54091-06-4), which is known as safener for rice against damage by some herbicides.

(15) Compounds, which are mainly used as herbicides, but which exhibit also safener activity on some crops, e.g. (2,4-dichlorophenoxy)acetic acid (2,4-D), (4-chlorophenoxy)acetic acid, (R,S)-2-(4-chlor-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl-3,6-dichloro-2-methoxybenzoate (lactidichlorethyl).

being plant growth regulators which may be mentioned are chlorocholine chloride and ethephon.

Examples of plant nutrients which may be mentioned are customary inorganic or organic fertilizers for supplying plants with macro- and/or micronutrients.

In a preferred embodiment the present invention relates to the use of a composition comprising A) fluopyram and B) one or more of the following insecticides:

Chlornicotinyls, preferably Imidacloprid, Clothianidin, Thiacloprid and Thiamethoxam Pyrethroids, preferably Lambda-Cyhalothrin, β-Cyfluthrin, Tefluthrin, Transfluthrin, Deltamethrin Carbamates, preferably Methiocarb, Thiodicarb and Aldicarb Organophosphates, preferably Fenamiphos, Fosthiazate, Ethoprofos.

Anthranilamids, preferably Rynaxypyr, Cyzazypyr

Macrolids, preferably Abamectin, Spinosad, Spinetoram

Fiproles, preferably Fipronil and Ethiprole

Additional nematicides, preferably Oxamyl

Ketoenols, preferably Spirotetramate, Spirodiclofen and Spiromesifen

4-[(2,2-difluoroethyl)amino]furan-2(5H)-one-2-chloro-5-Ethylpyridin (1:1), Sulfoxaflor, Flonicamid, flupyradifurone Fumigants, and biological control agents, preferably Pasteuria.

Nematodes

Fluopyram or fluopyram in combination with the biological control agent *Bacillus firmus* strain CNCM I-1582 or fluopyram in combination with at least one agrochemically active compound is particularly useful in controlling plant-parasitic nematodes in nematode-resistant plants wherein the nematodes are of the following species:

*Aphelenchoides* spp., *Bursaphelenchus* spp. *Ditylenchus* spp. *Globodera* spp., *Heterodera* spp., *Longidorus* spp., *Meloidogyne* spp., *Pratylenchus* spp., *Radopholus* spp., *Trichodorus* spp. *Tylenchulus* spp, *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp, *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp

*Aglenchus agricola, Anguina tritici, Aphelenchoides arachidis, Aphelenchoides fragariae, Belonolaimus gracilis, Belonolaimus longicaudatus, Belonolaimus nortoni, Cacopaurus pestis, Criconemella curvata, Criconemella onoensis, Criconemella ornata, Criconemella rusium, Criconemella xenoplax (=Mesocriconema xenoplax)* and *Criconemoides* spp. in general, *Criconemoides ferniae, Criconemoides onoense, Criconemoides ornatum* and *Criconemoides* spp. in general, *Ditylenchus destructor, Dity-*

*lenchus dipsaci, Ditylenchus myceliophagus* and *Ditylenchus* spp. in general, *Dolichodorus heterocephalus, Globodera pallida* (=*Heterodera pallida*), *Globodera rostochiensis, Globodera solanacearum, Globodera tabacum, Globodera virginiae, Helicotylenchus digonicus, Helicotylenchus dihystera, Helicotylenchus erythrine, Helicotylenchus multicinctus. Helicotylenchus nannus, Helicotylenchus pseudorobustus* and *Helicotylenchus* spp. in general, *Hemicriconemoides, Hemicycliophora arenaria, Hemicycliophora nudata, Hemicycliophora parvana, Heterodera avenae, Heterodera cruciferae, Heterodera glycines, Heterodera oryzae, Heterodera schachtii, Heterodera zeae* and *Heterodera* spp. in general, *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and *Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne naasi, Meloidogyne paranaensis, Meloidogyne thamesi* and *Meloidogyne* spp. in general, *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Parartylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and *Pratylenchus* spp. in general, *Pseudohalenchus minutus, Psilenchus magnidens, Psilenchus tumidus. Punctodera chalcoensis, Quinisulcius acutus, Radopholus citrophilus, Radopholus similis, Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and *Scutellonema* spp. in general, *Subanguina radiciola, Tetylenchus nicotianae, Trichodorus cyclindricus, Trichodorus minor, Trichodorus primitivus, Trichodorus proximus, Trichodorus similis, Trichodorus sparsus* and *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans, Xiphinema americanum, Xiphinema brevicolle, Xiphinema dimorphicaudatum, Xiphinema index* and *Xiphinema* spp Definition of Plant Parts According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, tubers, corms and rhizomes are listed. Crops and vegetative and generative propagating material, for example cuttings, corms, rhizomes, tubers, runners and seeds also belong to plant parts.

As already mentioned above, it is possible to treat all plants and their parts according to the invention. In one embodiment, wild plant species and plant cultivars, or those obtained by conventional biological breeding, such as crossing or protoplast fusion, and parts thereof, are treated. In a further embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

GMOs

Plants of the plant cultivars which are in each case commercially available or in use can be treated according to the invention. Plant cultivars are to be understood as meaning plants having novel properties ("traits") which can be obtained by conventional breeding, by mutagenesis or by recombinant DNA techniques. This can be varieties, bio- and genotypes.

The transgenic plants or plant cultivars (i.e. those obtained by genetic engineering) which can be treated according to the invention include all plants which, in the genetic modification, received genetic material which imparted particularly advantageous useful traits to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against nematodes, insects, mites, phytopathogenic fungi, bacteria and/or viruses, and also increased tolerance of the plants to certain herbicidal active compounds. Particular emphasis is given to vegetables, potato, corn, soy, cotton and banana.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance. Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776, 760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024, 782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421, 292, 11/400,598, 11/651,752, 11/681,285, 11/605,824, 12/468,205, 11/760,570, 11/762,526, 11/769,327, 11/769, 255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273, 894; 5,637,489; 5,276,268; 5,739,082; 5,908,810 and 7,112, 665.

Further herbicide-tolerant plants are also plants that are made tolerant to the herbicides inhibiting the enzyme hydroxyphenylpyruvatedioxygenase (HPPD). Hydroxyphenylpyruvatedioxygenases HPPD is an are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, and WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024,782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084, 082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab. Cry 1Ac, Cry 1B, Cry 1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or
5) an insecticidal secreted protein from *Bacillus thuringiensis* or *Bacillus cereus*, or an insecticidal portion thereof, such as the vegetative insecticidal (VIP) proteins listed at: http//www.lifesci.sussex.ac.uk/home/Neil_Crickmore/Bt/vip.html. e.g., proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or
9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).
10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126. WO 2006/129204. WO 2007/074405. WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:
1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734, 341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936
2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1, 4-glucans as disclosed in WO 95/31553, US 2002031826, U.S. Pat. No. 6,284,479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

- a) Plants, such as cotton plants, containing an altered form of cellulose synthase genes as described in WO 98/00549
- b) Plants, such as cotton plants, containing an altered form of rsw2 or rsw3 homologous nucleic acids as described in WO 2004/053219
- c) Plants, such as cotton plants, with increased expression of sucrose phosphate synthase as described in WO 01/17333
- d) Plants, such as cotton plants, with increased expression of sucrose synthase as described in WO 02/45485
- e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
- f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

- a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947
- b) Plants such as oilseed rape plants, producing oil having a low linolenic acid content as described in U.S. Pat. No. 6,270,828, U.S. Pat. No. 6,169,190, or U.S. Pat. No. 5,965,755
- c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as potatoes which are virus-resistant, e.g. against potato virus Y (event SY230 and SY233 from Tecnoplant, Argentina), which are disease resistant, e.g. against potato late blight (e.g. RB gene), which show a reduction in cold-induced sweetening (carrying the Nt-Inhh, IIR-INV gene) or which possess a dwarf phenotype (Gene A-20 oxidase).

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230, and EP 08075648.9, WO09/068,313 and WO10/006,732.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Formulations

Suitable extenders and/or surfactants which may be contained in the compositions according to the invention are all formulation auxiliaries which can customarily be used in plant treatment compositions.

In the compositions according to the invention the ratio of fluopyram to an agrochemically active compound of group (B) can be varied within a relatively wide range. In general, between 0.02 and 2.0 parts by weight, preferably between 0.05 and 1.0 part by weight, of fluopyram is employed per part by weight of agrochemically active compound.

When employing the active compounds of the formula (I) which can be used according to the invention, the application rates can be varied within a certain range, depending on the type of application. In the treatment of seed, the application rates of active compound of the formula (I) are generally between 10 and 10000 mg per kilogram of seed, preferably between 10 and 300 mg per kilogram of seed. When used in solid formulations, the application rates of active compound of the formula (I) are generally between 20 and 800 mg per kilogram of formulation, preferably between 30 and 700 mg per kilogram of formulation.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, and also protein hydrolysates. Suitable dispersants are: for example lignosulphite waste liquors and methylcellulose.

Suitable liquefied gaseous extenders or carriers are liquids which are gaseous at ambient temperature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.05 and 99 percent by weight of the active compound combination according to the invention, preferably between 10 and 70 percent by weight, particularly preferably between 20 and 50 percent by weight, most preferably 25 percent by weight.

The active compound combinations or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

Organic diluents that may be present are all polar and non-polar organic solvents that are customarily used for such purposes. Preferred are ketones, such as methyl isobutyl ketone and cyclohexanone, furthermore amides, such as dimethylformamide and alkanecarboxamides, such as N,N-dimethyldecanamide and N,N-dimethyloctanamide, furthermore cyclic compounds, such as N-methylpyrrolidone, N-octylpyrrolidone. N-dodecylpyrrolidone, N-octylcaprolactam, N-dodecylcaprolactam and butyrolactone, additionally strongly polar solvents, such as dimethyl sulphoxide, furthermore aromatic hydrocarbons, such as xylene, Solvesso™, mineral oils, such as white spirit, petroleum, alkylbenzenes and spindle oil, moreover esters, such as propylene glycol monomethyl ether acetate, dibutyl adipate, hexyl acetate, heptyl acetate, tri-n-butyl citrate and di-n-butyl phthalate, and furthermore alcohols, such as, for example, benzyl alcohol and 1-methoxy-2-propanol.

Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable surfactants (adjuvants, emulsifiers, dispersants, protective colloids, wetting agents and tackifiers) are customary ionic and nonionic substances. Examples which may be mentioned are ethoxylated nonylphenols, polyalkylene glycol ethers of straight-chain or branched alcohols, products of reactions of alkylphenols with ethylene oxide and/or propylene oxide, products of reactions of fatty amines with ethylene oxide and/or propylene oxide, furthermore fatty esters, alkylsulphonates, alkyl sulphates, alkyl ether sulphates, alkyl ether phosphates, aryl sulphates, ethoxylated arylalkylphenols, such as, for example, tristyrylphenol ethoxylates, furthermore ethoxylated and propoxylated arylalkylphenols and also sulphated or phosphated arylalkylphenol ethoxylates or ethoxy- and propoxylates. Mention may furthermore be made of natural and synthetic water-soluble polymers, such as lignosulphonates, gelatine, gum arabic, phospholipids, starch, hydrophobically modified starch and cellulose derivatives, in particular cellulose esters and cellulose ethers, furthermore polyvinyl alcohol, polyvinyl acetate, polyvinylpyrrolidone, polyacrylic acid, polymethacrylic acid and copolymers of (meth)acrylic acid and (meth)acrylic acid esters, and moreover also alkali metal hydroxide-neutralized copolymers of methacrylic acid and methacrylic ester and condensates of optionally substituted naphthalenesulphonic acid salts with formaldehyde.

Suitable solid fillers and carriers are all substances customarily used for this purpose in crop protection compositions. Inorganic particles, such as carbonates, silicates, sulphates and oxides having a mean particle size of from 0.005 to 20 µm, particularly preferably from 0.02 to 10 µm, may be mentioned as being preferred. Examples which may be mentioned are ammonium sulphate, ammonium phosphate, urea, calcium carbonate, calcium sulphate, magnesium sulphate, magnesium oxide, aluminium oxide, silicon dioxide, finely divided silicic acid, silica gels, natural and synthetic silicates and alumosilicates and vegetable products such as cereal meal, wood powder and cellulose powder.

Suitable colorants that may be present in the seed dressing formulations to be used according to the invention include all colorants customary for such purposes. Use may be made both of pigments, of sparing solubility in water, and of dyes, which are soluble in water. Examples that may be mentioned include the colorants known under the designations Rhodamin B, C.I. Pigment Red 112 and C.I. Solvent Red 1. The colorants used can be inorganic pigments, for example iron oxide, titanium oxide, Prussian Blue, and organic dyes, such as alizarin, azo and metal phthalocyanine dyes, and trace nutrients, such as salts of iron, manganese, boron, copper, cobalt, molybdenum and zinc.

Suitable wetting agents that may be present in the seed dressing formulations to be used according to the invention include all substances which promote wetting and are customary in the formulation of agrochemically active compounds. Preference is given to using alkylnaphthalenesulphonates, such as diisopropyl- or diisobutylnaphthalenesulphonates.

Suitable dispersants and/or emulsifiers that may be present in the seed dressing formulations to be used according to the invention include all nonionic, anionic and cationic dispersants which are customary in the formulation of agrochemically active compounds. Preference is given to using nonionic or anionic dispersants or mixtures of nonionic or anionic dispersants. Particularly suitable nonionic dispersants are ethylene oxide/propylene oxide block polymers, alkylphenol polyglycol ethers, and also tristryrylphenol polyglycol ethers and their phosphated or sulphated derivatives. Particularly suitable anionic dispersants are lignosulphonates, polyacrylic acid salts and arylsulphonate/formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Agents and Pesticides], Vol. 2. Springer Verlag, 1970, pp. 401-412).

The formulations generally comprise between 0.1 and 95% by weight of active compound, preferably between 0.5 and 90%.

The active compound combinations according to the invention can be present in commercial formulations and in the use forms prepared from these formulations as a mixture with other active compounds, such as insecticides, attractants, sterilants, bactericides, acaricides, nematicides, fungicides, growth regulators or herbicides. A mixture with fertilizers is also possible.

The treatment according to the invention of the plants and plant parts with the active compound combinations or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. Preference is given to application by dipping, spraying, atomizing, irrigating, evaporating, dusting, fogging, broadcasting, foaming, painting, spreading-on, watering (drenching) and drip irrigating.

The application of the formulations is carried out in accordance with customary agricultural practice in a manner adapted to the application forms. Customary applications are, for example, dilution with water and spraying of the resulting spray liquor, application after dilution with oil, direct application without dilution, seed dressing or soil application of carrier granules.

The active compound content of the application forms prepared from the commercial formulations can vary within wide limits. The active compound concentration of the application forms can be from 0.0000001 up to 95% by weight of active compound, preferably between 0.0001 and 2% by weight.

The compositions according to the invention do not only comprise ready-to-use compositions which can be applied with suitable apparatus to the plant or the seed, but also commercial concentrates which have to be diluted with water prior to use.

Application Methods

The treatment according to the invention of the plants and plant parts with Fluopyram or compositions is carried out directly or by action on their surroundings, habitat or storage space using customary treatment methods, for example by dipping, spraying, atomizing, irrigating, stem injection, in-furrow application, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compounds by the ultra-low volume method, or to inject the active compound preparation or the active compound itself into the soil.

Generally, fluopyram is applied in a rate of 10 g to 20 kg per ha, preferably 50 g to 10 kg per ha, most preferably 100 g to 5 kg per ha.

The invention furthermore comprises a method for treating seed. The invention furthermore relates to seed treated according to one of the methods described in the preceding paragraph.

Fluopyram or compositions comprising fluopyram according to the invention are especially suitable for treating seed. A large part of the damage to crop plants caused by harmful organisms is triggered by an infection of the seed during storage or after sowing as well as during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of nematodes by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or which at least considerably reduce additional application. It is furthermore desirable to optimize the amount of active compound employed in such a way as to provide maximum protection for the seed and the germinating plant from attack by nematodes, but without damaging the plant itself by the active compound employed. In particular, methods for the treatment of seed should also take into consideration the intrinsic nematicidal properties of transgenic plants in order to achieve optimum protection of the seed and the germinating plant with a minimum of crop protection agents being employed.

Accordingly, the present invention also relates in particular to a method for protecting seed and germinating plants against attack by nematodes by treating the seed with Fluopyram or a composition comprising fluopyram according to the invention. The invention also relates to the use of the compositions according to the invention for treating seed for protecting the seed and the germinating plant against nematodes. Furthermore, the invention relates to seed treated with a composition according to the invention for protection against nematodes.

The control of nematodes which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

One of the advantages of the present invention is that, because of the particular systemic properties of Fluopyram or a composition comprising fluopyram according to the invention, treatment of the seed with Fluopyram or these compositions not only protects the seed itself, but also the resulting plants after emergence, from nematodes. In this manner, the immediate treatment of the crop at the time of sowing or shortly thereafter can be dispensed with.

Fluopyram or the compositions comprising fluopyram according to the invention are suitable for protecting seed of vegetables, in particular tomato and cucurbits, potato, corn, soy, cotton, tobacco, coffee, fruits, in particular, citrus fruits, pine apples and bananas, and grapes.

As also described further below, the treatment of transgenic seed with Fluopyram or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

In the context of the present invention, Fluopyram or a composition comprising fluopyram according to the invention are applied on their own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of Fluopyram or a composition comprising fluopyram according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

Fluopyram or a composition comprising fluopyram according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

Fluopyram or a composition comprising fluopyram which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

Suitable wetting agents that may be present in the seed dressing formulations which can be used according to the invention include all substances which promote wetting and are customary in the formulation of active agrochemical substances. With preference it is possible to use alkylnaphthalene-sulphonates, such as diisopropyl- or diisobutylnaphthalene-sulphonates.

Suitable dispersants and/or emulsifiers that may be present in the seed dressing formulations which can be used according to the invention include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Agents and Pesticides], Vol. 2, Springer Verlag, 1970, pp. 401-412).

The seed dressing formulations which can be used according to the invention may be used directly or after dilution with water beforehand to treat seed of any of a very wide variety of types. The seed dressing formulations which can be used according to the invention or their dilute preparations may also be used to dress seed of transgenic plants. In this context, synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The nematicidal compositions according to the invention can be used for the curative or protective control of nematodes. Accordingly, the invention also relates to curative and protective methods for controlling nematodes using the fluopyram and compositions containing fluopyram according to the invention, which are applied to the seed, the plant or plant parts, the fruit or the soil in which the plants grow. Preference is given to application onto the plant or the plant parts, the fruits or the soil.

The compositions according to the invention for controlling nematodes in crop protection comprise an active, but non-phytotoxic amount of the compounds according to the invention. "Active, but non-phytotoxic amount" shall mean an amount of the composition according to the invention which is sufficient to control or to completely kill the plant disease caused by nematodes, which amount at the same time does not exhibit noteworthy symptoms of phytotoxicity. These application rates generally may be varied in a broader range, which rate depends on several factors, e.g. the nematodes, the plant or crop, the climatic conditions and the ingredients of the composition according to the invention.

The fact that the active compounds, at the concentrations required for the controlling of plant diseases, are well tolerated by plants permits the treatment of aerial plant parts, of vegetative propagation material and seed, and of the soil.

In an exemplary seed treatment method, an aqueous composition comprising fluopyram can be applied at a rate to provide in the range of 0.5 g to 10 kg, preferably 0.8 g to 5 kg, most preferably 1 g to 1 kg Fluopyram per 100 kg (dt) of seeds.

In an exemplary seed treatment method, an aqueous composition comprising the biological control agent, in particular *Bacillus firmus* CNCM I-1582 spore can be applied at a rate to provide in the range of 0.1 g to 20 g, preferably 1 g to 10 g, particularly preferably 2.5 g to 7.5 g., and most preferably approximately 5 g Bacillus firmus CNCM I-1582 spore per hectare or 100.000 kernels of seed. The above ranges refer to a spore formulation or suspension containing $10^{11}$ spores/g.

In various embodiments, the biological control agent is added to the seed at a rate of about $1\times10^5$ to $1\times10^8$ colony forming units (cfu) per seed, including about $1\times10^5$ cfu/seed, or about $1\times10^6$ cfu/seed, or about $1\times10^7$ cfu/seed, or about $1\times10^8$ cfu/seed, including about $1\times10^5$ to $1\times10^7$ cfu/per seed, about $1\times10^5$ to $1\times10^6$ cfu/per seed, about $1\times10^6$ to $1\times10^8$ cfu/per seed, about $1\times10^6$ to $1\times10^7$ cfu/per seed and about $1\times10^7$ to $1\times10^8$ cfu/per seed.

The general concepts of the invention are described in the following examples, which are not to be considered as limiting.

EXAMPLE 1

Two tests were planted with Jack (an SCN resistant soybean variety with PI 88788 resistance) and two genetically modified Jack varieties (AXN2 and AXMI031) known to produce a nematicidal protein. The seed were treated with a color/coating base or the same base plus one of two different rates of fluopyram (experiment 1 used 0.075 mg fluopyram/seed and experiment 2 used 0.15 mg fluopyram/seed). The SCN used to inoculate both tests were collected from an inbred colony (OP50) with the ability to overcome PI 88788 resistance.

Tests were conducted as non-randomized blocks with a minimum of 10 replicates. Seed were planted in individual 4" clay pots with coarse sand and inoculated with approximately 20,000 OP50 juveniles in ten equal inoculations beginning at planting and again approximately every third day. Plants were maintained in a germination chamber. Blocks were rotated approximately every third day to minimize potential influence of environmental variance. Two months after planting, plants were harvested and cysts were collected and counted to evaluate the efficacy of the nematicide and traits, both individually and in combination with each other.

With the base treatment (color/coating), about half way through the project a reduction in height was recorded with both of the genetically modified varieties compared to the non-transformed plants.

Fluopyramn (AR83685) has not been shown to provide a positive growth response, which was also observed in the nontransgenic Jack plants in this experiment. However, fluopyram increased average plant height on both genetically modified varieties in both experiments while not having an effect on the nontransgenic control plants. Thus, while not being bound by any particular theory or mechanism, it appears as though the application of fluopyram to the transgenic Axn2 and Axmi031 plants overcame the growth inhibitory effects resulting from the presence of the transgene. There were no growth-promoting effects in the nontransgenic control, nor in the untreated transgenic plants.

In both experiments (0.075 mg fluopyram/seed and 0.15 mg fluopyram/seed) the average number of cysts collected from Jack plants with the base (color/coating) treatment was relatively consistent (1310 and 1190 cysts). When comparing these averages to those from the AXMI031 plants (also with the base treatment), the percent reductions were also very consistent (92% and 88%). As for the AXN2 plants (again with the base treatment), the individual results in the second experiment were highly variable and in the end the overall percent reduction (as compared to the Jack) was significantly higher (43%) as compared to the first experiment (20%). See FIG. 1.

In the first experiment the fluopyram (0.075 mg/seed) reduced SCN populations by 26% on the nontransgenic Jack plants. When the rate of the chemical was doubled in the second experiment (0.15 mg fluopyram/seed), the reduction almost doubled as well (43%). Considering this is an experimental nematicide the limiting factor was likely not SCN immune to the effects of the chemical but more likely its distribution within the rhizosphere and the number of SCN which were exposed to a lethal concentration.

Figure 2:
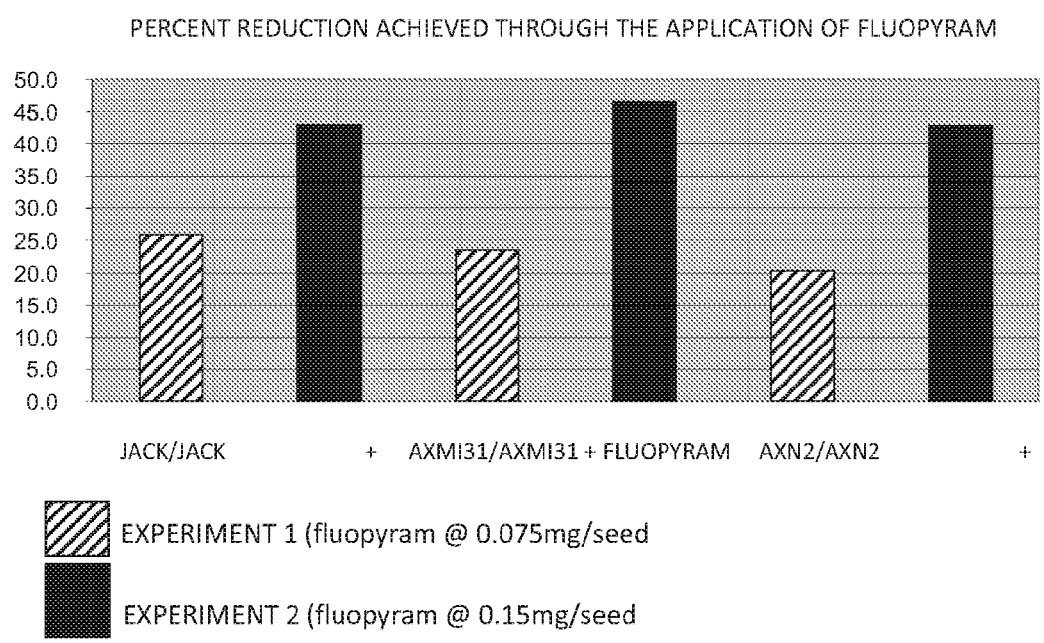

Based on that assumption, the percent control attributable to fluopyram would be expected to be less with the transgenic seed due to a potential overlap (e.g., fewer nematodes available for targeting by the fluopyram). However, the control achieved through the traits (20/43%-AXN2; 92/88%-AXMI31) did not diminish the effects of fluopyram. Fluopyram provided an approximate reduction of 20% at the low rate and an approximate reduction of 40% at the high rate for both Axmi031 and Axn2 Thus, fluopyram resulted in a consistent level of nematode control despite the significantly lower nematode pressure resulting from the presence of the transgene (FIG. 2).

The invention claimed is:

1. A method for controlling nematodes infesting a nematode resistant plant and/or increasing crop yield in a nematode resistant plant comprising applying N-{2-[3-chloro-5-(trifluoromethyl)-2-pyridinyl]ethyl}-2-(trifluoromethyl)benzamide (fluopyram) of formula (I)

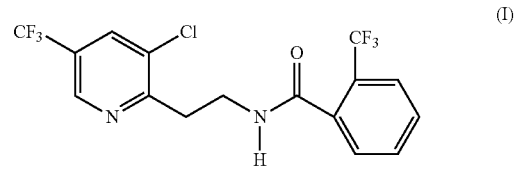 [SMILES: O=C(NCCc1ncc(C(F)(F)F)cc1Cl)c1ccccc1C(F)(F)F]

and/or N-oxides thereof to a nematode resistant plant, plant part, seed, or soil, to thereby control nematode infestation and/or increase crop yield in the nematode resistant plant, wherein the nematode resistant plant carries one or more genes selected from axmi205; optaxmi205v01.03; optaxmi205v01.02; optaxmi205v01.04; optaxmiR1(evo 21); optaxmiR1 (evo 22); optaxmiR1(evo 23); optaxmiR1(evo 26); optaxmi115v01; optaxmi115v02; axmi115v02; axmi100; axmi076; axmi005; optcry1Ac; axmi031; axn2; Hs1$^{pro-1}$, Mi-1, Mi-1.2, Hero A, Gpa 2, Gro1-4, Rhg1, Rhg4, Mi-3, Mi-9, Cre1, Cre3, Ma, Hsa-1$^{Og}$, Me3, Rmc1, and CLAVATA3-like peptides.

2. The method according to claim 1, further comprising applying at least one agrochemically active compound in addition to fluopyram,
and one or more extenders and/or surfactants,
to the nematode resistant plant, plant part, seed, or soil, to thereby control nematode infestation and/or increase crop yield in the nematode resistant plant.

3. The method according to claim 1, wherein the nematodes controlled are phytoparasitic nematodes of the genera *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp, *Xiphinema* spp., *Helicotylenchus* spp., *Tylenchorhynchus* spp., *Scutellonema* spp.,

*Paratrichodorus* spp., *Meloinema* spp., *Paraphelenchus* spp., *Aglenchus* spp., *Belonolaimus* spp., *Nacobbus* spp, *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., and/or *Cacopaurus* spp.

4. A method according to claim 1, wherein fluopyram is applied in a rate of 100 g to 5 kg per ha.

5. The method according to claim 1, wherein fluopyram is applied to a crop seed for control of nematodes in the nematode resistant plant, wherein the crops are selected from the group consisting of tomato, cucurbits, potato, corn, soy, cotton, tobacco, coffee, citrus fruits, pine apples, bananas, and grapes.

6. The method according to claim 2, wherein the at least one agrochemically active compound comprises *Bacillus firmus* strain CNCM 1-1582.

7. The method according to claim 1, wherein fluopyram is applied to a seed of the nematode resistant plant.

8. The method according to claim 7, wherein fluopyram is applied at a rate of 10 to 10,000 mg per kilogram of seed.

9. The method according to claim 7, wherein fluopyram is applied at a rate of 10 to 300 mg per kilogram of seed.

10. The method according to claim 1, wherein the nematode resistant plant comprises a transgenic plant comprising Axmi031 or Axn2.

11. The method according to claim 2, wherein 0.02 to 2.0 parts by weight of fluopyram is applied per part by weight of the at least one agrochemically active compound.

12. The method according to claim 2, wherein 0.05 to 1.0 parts by weight of fluopyram is applied per part by weight of the at least one agrochemically active compound.

13. A method according to claim 2, wherein fluopyram and the at least one agrochemically active compound are applied at a rate of 100 g to 5 kg per ha.

14. The method according to claim 2, wherein fluopyram and the at least one agrochemically active compound are applied to a seed of a nematode resistant plant.

15. The method according to claim 2, wherein fluopyram and the at least one agrochemically active compound are applied to a crop for control of nematodes in nematode resistant plant, wherein the crops are selected from the group consisting of tomato, cucurbits, potato, corn, soy, cotton, tobacco, coffee, citrus fruits, pine apples, bananas, and grapes.

16. A nematode resistant plant treated with fluopyram wherein the nematode resistant plant carries one or more genes selected from axmi205; optaxmi205v01.03; optaxmi205v01.02; optaxmi205v01.04; optaxmiR1(evo 21); optaxmiR1(evo 22); optaxmiR1(evo 23); optaxmiR1(evo 26); optaxmi115v01; optaxmi115v02; axmi115v02; axmi100; axmi076; axmi005; optcry1Ac; axmi031; axn2; $Hs1^{pro-1}$, Mi-1, Mi-1.2, Hero A, Gpa 2, Gro1-4, Rhg1, Rhg4, Mi-3, Mi-9, Cre1, Cre3, Ma, $Hsa-1^{Og}$, Me3, Rmc1, and CLAVATA3-like peptides;

wherein the plant is effective in controlling nematodes infesting the nematode resistant plant and/or increasing crop yield in the nematode resistant plant.

17. The seed of a nematode-resistant plant treated with fluopyram wherein the nematode resistant plant carries one or more genes selected from axmi205; optaxmi205v01.03; optaxmi205v01.02; optaxmi205v01.04; optaxmiR1(evo 21); optaxmiR1(evo 22); optaxmiR1(evo 23); optaxmiR1(evo 26); optaxmi115v01; optaxmi115v02; axmi115v02; axmi100; axmi076; axmi005; optcry1Ac; axmi031; axn2; $Hs1^{pro-1}$, Mi-1, Mi-1.2, Hero A, Gpa 2, Gro1-4, Rhg1, Rhg4, Mi-3, Mi-9, Cre1, Cre3, Ma, $Hsa-1^{Og}$, Me3, Rmc1, and CLAVATA3-like peptides;

wherein the seed is effective in controlling nematodes infesting the nematode resistant plant and/or increasing crop yield in the nematode resistant plant.

18. A composition effective in controlling nematodes infesting a nematode resistant plant and/or increasing crop yield in a nematode resistant plant comprising:

A) fluopyram and

B) *Bacillus firmus* strain CNCM I-1582 wherein the nematode resistant plant carries one or more genes selected from axmi205; optaxmi205v01.03; optaxmi205v01.02; optaxmi205v01.04; optaxmiR1(evo 21); optaxmiR1 (evo 22); optaxmiR1(evo 23); optaxmiR1(evo 26); optaxmi115v01; optaxmi115v02; axmi115v02; axmi100; axmi076; axmi005; optcry1Ac; axmi031; axn2; $Hs1^{pro-1}$, Mi-1, Mi-1.2, Hero A, Gpa 2, Gro1-4, Rhg1, Rhg4, Mi-3, Mi-9, Cre1, Cre3, Ma, $Hsa-1^{Og}$, Me3, Rmc1, and CLAVATA3-like peptides; wherein the composition is in an effective amount to control nematodes infesting the nematode resistant plant and/or to increase crop yield in the nematode resistant plant.

* * * * *